(12) United States Patent
Iwakata et al.

(10) Patent No.: US 12,083,308 B2
(45) Date of Patent: *Sep. 10, 2024

(54) MALE CONNECTING DEVICE FOR MEDICAL USE

(71) Applicant: KOYO SANGYO CO., LTD., Tokyo (JP)

(72) Inventors: Mario Iwakata, Niigata (JP); Hiroki Watanabe, Niigata (JP); Takayuki Miyazaki, Niigata (JP)

(73) Assignee: KOYO SANGYO CO., LTD., Tokyo (JP)

( * ) Notice: Subject to any disclaimer, the term of this patent is extended or adjusted under 35 U.S.C. 154(b) by 923 days.

This patent is subject to a terminal disclaimer.

(21) Appl. No.: 17/054,377

(22) PCT Filed: Aug. 30, 2019

(86) PCT No.: PCT/JP2019/034165
§ 371 (c)(1),
(2) Date: Nov. 10, 2020

(87) PCT Pub. No.: WO2020/071024
PCT Pub. Date: Apr. 9, 2020

(65) Prior Publication Data
US 2021/0213271 A1    Jul. 15, 2021

(30) Foreign Application Priority Data
Oct. 4, 2018    (JP) .................................. 2018-188958

(51) Int. Cl.
*A61M 39/10*    (2006.01)

(52) U.S. Cl.
CPC . *A61M 39/1011* (2013.01); *A61M 2039/1033* (2013.01); *A61M 2039/1083* (2013.01);
(Continued)

(58) Field of Classification Search
CPC .............. A61M 39/1011; A61M 39/10; A61M 39/1055; A61M 2039/1033;
(Continued)

(56) References Cited

U.S. PATENT DOCUMENTS 6,152,913 A * 11/2000 Feith .................. A61M 39/1011
604/533
2008/0172039 A1    7/2008 Raines
(Continued)

FOREIGN PATENT DOCUMENTS

CN        106232173 A    12/2016
EP           3108926 A1    12/2016
(Continued)

OTHER PUBLICATIONS

Japan Patent Office, International Preliminary Report on Patentability for corresponding International Application No. PCT/JP2019/034165, mailed Apr. 15, 2021.
(Continued)

*Primary Examiner* — Laura A Bouchelle
*Assistant Examiner* — Sarah Dympna Grasmeder
(74) *Attorney, Agent, or Firm* — Jodi A. Reynolds, Esq.; Harter Secrest & Emery LLP

(57) ABSTRACT

A male connecting device for medical use 1 includes a male connector 10 having a cylindrical configuration and a threadedly engageable cylinder 20 rotatably coupled to the male connector 10. A male luer portion 11 of the male connector 10 and a female luer portion 2a of the female connector 2 are joined by turning the threadedly engageable cylinder 20 in a tightening direction T. The male connecting device 1 further includes a loosening prevention mechanism 40 that prohibits rotation of the threadedly engageable cylinder 20 in a loosening direction L with respect to the male connector 10. The loosening prevention mechanism 40
(Continued)

includes ratchet teeth 41 formed in an inner periphery of the threadedly engageable cylinder 20, an elastic leaf 42 formed in the male connector 10 and extends in a circumferential direction and an engageable claw 43 protruded from a free end of the elastic leaf 42 and engageable with the ratchet teeth 41.

8 Claims, 11 Drawing Sheets

(52) U.S. Cl.
CPC ............... *A61M 2039/1088* (2013.01); *A61M 2205/0216* (2013.01)

(58) Field of Classification Search
CPC .. A61M 2039/1044; A61M 2039/1038; A61M 2039/229; A61M 2205/0216; F16L 19/025; F16L 19/005
See application file for complete search history.

(56) References Cited

U.S. PATENT DOCUMENTS

| | | | |
|---|---|---|---|
| 2008/0287920 | A1 | 11/2008 | Fangrow et al. |
| 2009/0218813 | A1* | 9/2009 | Helstern ................ F16L 15/08 16/108 |
| 2013/0076030 | A1* | 3/2013 | Fog .......................... F16L 19/07 285/362 |
| 2014/0265312 | A1 | 9/2014 | McAlister |
| 2017/0120032 | A1* | 5/2017 | Miyazaki ............... A61M 39/10 |

FOREIGN PATENT DOCUMENTS

| | | |
|---|---|---|
| JP | S48-023058 | 7/1973 |
| JP | S56-006499 | 1/1981 |
| JP | S59-087840 | 6/1984 |
| JP | H09-182878 A | 7/1997 |
| JP | 2010-527276 A | 8/2010 |
| WO | 2016/157974 A1 | 10/2016 |

OTHER PUBLICATIONS

Chinese Patent Office, Office Action dated Jan. 18, 2022 with English translation.

Japan Patent Offce, International Search Report from corresponding International Patent Application No. PCT/JP2019/034165, mailed Nov. 19, 2019.

European Patent Office, Extended European Search Report for corresponding European patent application No. 19868995.2 dated Jan. 5, 2022.

* cited by examiner

MALE CONNECTING DEVICE FOR MEDICAL USE

FIELD OF THE INVENTION

The present invention relates to a male connecting device used in cooperation with a female connector to connect medical components such as tubes.

BACKGROUND OF THE INVENTION

There are various types of connecting structures for connecting medical components such as tubes. A connecting structure of the kind disclosed in Patent Document 1 to be described later includes a male connecting device 1 and a female connector 2 as shown in FIGS. 13 and 14.

The male connecting device 1 includes a male connector 10 and a threadedly engageable cylinder 20 rotatably attached to the male connector 10. The threadedly engageable cylinder 20 includes a threadedly engageable portion 21 disposed outside of a male luer portion 11 of the male connector 10 in a radial direction. A female screw 21a is formed in an inner periphery of the threadedly engageable portion 21.

The female connector 2 includes a female luer portion 2a. Engageable protrusions 2c threadedly engageable with the female screw 21a are formed in an outer periphery of a distal end portion of the female luer portion 2a.

As shown in FIG. 13, when the threadedly engageable cylinder 20 is turned in a tightening direction in a state where the female screw 21a of the threadedly engageable cylinder 20 and the engageable protrusions 2c of the female connector 2 are threadedly engaged with each other, the male luer portion 11 and the female luer portion 2a are joined. When the threadedly engageable cylinder 20 is turned further in the tightening direction, the male luer portion 11 and the female luer portion 2a are tightly joined with a pressing force working therebetween, providing sufficient sealing properties.

When the threadedly engageable cylinder 20 is in a tightened state as shown in FIG. 13, a surface 21x on a deeper side of a screw thread of the female screw 21a is strongly abutted against the engageable protrusions 2c, thereby drawing the female luer portion 2a toward the male luer portion 11. By friction between the surface 21x on the deeper side of the screw thread of the female screw 21a and the engageable protrusions 2c, the threadedly engageable cylinder 20 keeps the female luer portion 2a in the drawn state, thereby keeping the male luer portion 11 and the female luer portion 2a in the joined state.

However, as shown in FIG. 13, there is a gap G in an axial direction between a surface 21y on an open end side of the screw thread of the female screw 21a and the engageable protrusions 2c, and by vibration or unintentional application of torque, the threadedly engageable cylinder 20 may be rotated through an angle corresponding to the gap G in a loosening direction as shown in FIG. 14. This causes the surface 21y on the open end side of the screw thread of the female screw 21a to be abutted against the engageable protrusions 2c, thereby forming a gap G between the surface 21x on the deeper side of the screw thread and the engageable protrusions 2c. When liquid flows in the connecting structure in this condition, pressure of the fluid causes the male luer portion 11 and the female luer portion 2a to be displaced in a separating direction through a distance corresponding to the gap G. As a result, sufficient sealing properties may not be achieved, causing the liquid to leak from between the male luer portion 11 and the female luer portion 2a.

A connecting structure for medical use including a torque limiting mechanism developed by the inventors of the present application is disclosed in FIGS. 1 to 6 of the Patent Document 2 to be described later. In the connecting structure for medical use, as with the connecting structure shown in FIGS. 13 and 14 mentioned above, a threadedly engageable cylinder is not prohibited from rotating in a loosening direction.

A loosening prevention mechanism disposed between a male connector and a threadedly engageable cylinder is disclosed in FIGS. 73 to 75 of Patent Document 3 to be described later. The loosening prevention mechanism prohibits loosening of the threadedly engageable cylinder by engagements of a lot of first engageable protrusions formed in an inner periphery of the threadedly engageable cylinder over an entire periphery and second engageable protrusions formed in an outer periphery of the male connector.

PRIOR ART DOCUMENT

Patent Document

Patent Document 1: Japanese Utility Model Application Publication No. S59-87840

Patent Document 2: International Patent Application Publication No. WO2016/157974

Patent Document 3: Japanese Patent Application Publication No. 2010-527276

SUMMARY OF THE INVENTION

Problem to be Solved by the Invention

In the connecting structure for medical use disclosed in Patent Document 3, when the threadedly engageable cylinder is turned in a tightening direction to join a male luer portion and a female luer portion, the loosening prevention mechanism poses a relatively high resistance, hindering smooth joining work.

Means for Solving the Problems

To solve the problems mentioned above, the present invention provides a male connecting device for medical use including a male connector having a cylindrical configuration and a threadedly engageable cylinder rotatably coupled to the male connector, the male connector including a male luer portion and a support portion arranged in a direction from a distal end to a basal end thereof in this order, the threadedly engageable cylinder including a threadedly engageable portion and a mounting portion arranged in a direction from a distal end to a basal end thereof in this order, the mounting portion of the threadedly engageable cylinder rotatably mounted on an outer periphery of the support portion of the male connector, the threadedly engageable portion including a female screw in an inner periphery thereof, the threadedly engageable portion disposed outside of the male luer portion in a radial direction, wherein the male connecting device further includes a loosening prevention mechanism disposed between the male connector and the threadedly engageable cylinder, the loosening prevention mechanism prohibits the threadedly engageable cylinder from rotating in a loosening direction with respect to the male connector, wherein the loosening prevention mechanism includes ratchet teeth formed in an inner periphery of the threadedly engageable cylinder over an entire periphery, at least one elastic leaf formed in an outer periphery of the male connector so as to extend in a circumferential direction with a free end thereof spaced from the outer periphery of the male connector and an engageable claw formed in the free end of the elastic leaf so as to be protruded outward in a radial direction, wherein when the threadedly engageable cylinder receives a rotary torque in a tightening direction, the engageable claw is moved over the ratchet teeth accompanied by an elastic deformation of the elastic leaf inward in the radial direction, thereby allowing the threadedly engageable cylinder to be rotated with respect to the male connector, and when the threadedly engageable cylinder receives a rotary torque in the loosening direction, the engageable claw catches the ratchet teeth, thereby prohibiting the threadedly engageable cylinder from rotating with respect to the male connector.

According to the features mentioned above, in a state where the male luer portion is joined with a female lure portion of a female connector, the threadedly engageable cylinder can be prohibited from loosening with respect to the male connector by engagement of the engageable claw and the ratchet teeth of the loosening prevention mechanism, thereby the luer portions can be maintained in a good joined state. When the threadedly engageable cylinder is tightened, the engageable claw is moved over a corresponding tooth of the ratchet teeth of the threadedly engageable cylinder accompanied by the elastic deformation of the elastic leaf inward in the radial direction. Therefore, a high resistance is not generated, and the joining work can be performed smoothly. Furthermore, since the elastic leaves extend in the circumferential direction, twisting force is not applied to the elastic leaves when a rotary torque in a tightening direction or a loosening direction is applied to the threadedly engageable cylinder. Therefore, strength of the elastic leaves can be maintained.

Preferably, the elastic leaf extends in the tightening direction of the threadedly engageable cylinder.

According to the features mentioned above, the elastic leaves can be easily elastically deformed when a rotary torque in the tightening direction is applied to the threadedly engageable cylinder, and the joining work can be performed further smoothly. The engagements of the engageable claws and the ratchet teeth are deepened when a rotary torque in the loosening direction is applied to the threadedly engageable cylinder, the threadedly engageable cylinder can be further surely prevented from loosening with respect to the male connector.

Preferably, a support protrusion protruded outward in the radial direction is formed in the outer periphery of the male connector and the elastic leaf extends from a distal end of the support protrusion in the circumferential direction.

According to the features mentioned above, the elastic leaves can be easily elastically deformed when the threadedly engageable cylinder is turned in the tightening direction, and the joining work can be performed further smoothly.

Preferably, a chamfered flat surface is formed in the outer periphery of the male connector, the support protrusion continues from an end portion of the flat surface in the circumferential direction, and the elastic leaf extends along the flat surface and is spaced from the flat surface.

According to the features mentioned above, the elastic leaves can be elastically deformed inward in the radial direction without being significantly protruded outward in the radial direction from the outer periphery of the male connector.

Preferably, a reinforcement raised portion that continues to the support protrusion is formed in the outer periphery of the male connector on an opposite side to the elastic leaf.

According to the features mentioned above, even when a strong rotary torque is applied to the threadedly engageable cylinder and a strong force toward the support protrusion is applied to the elastic leaf, the strong force can be received by the reinforcement raised portion. Thereby, strength of the elastic leaf and the support protrusion can be surely maintained.

Preferably, the male connecting device for medical use further includes an operation cylinder rotatably mounted on an outer periphery of the threadedly engageable cylinder and a torque limiting mechanism disposed between the threadedly engageable cylinder and the operation cylinder, wherein the torque limiting mechanism transmits a rotary torque of the operation cylinder in a tightening direction to the threadedly engageable cylinder, the torque limiting mechanism allows the operation cylinder to be turned idly with respect to the threadedly engageable cylinder when the rotary torque exceeds a predetermined torque, the torque limiting mechanism includes engageable teeth formed in an inner periphery of the operation cylinder over an entire periphery, at least one elastically deformable portion formed in the threadedly engageable cylinder and a second engageable claw formed in the elastically deformable portion and protruded outward in the radial direction, the second engageable claw engageable with the engageable teeth, and an elastic coefficient of the elastically deformable portion is higher than an elastic coefficient of the elastic leaf of the loosening prevention mechanism.

According to the features mentioned above, an excessive torque is not applied to the threadedly engageable cylinder, and an inconvenient situation such as the male luer portion and the female luer portion being inseparably locked with each other can be prevented.

Preferably, the elastically deformable portion is formed in an end portion of the mounting portion of the threadedly engageable cylinder and the ratchet teeth of the loosening prevention mechanism are formed in an inner periphery of the mounting portion at locations adjacent to the elastically deformable portion in an axial direction.

Advantageous Effects of the Invention

According to the present invention, the loosening prevention mechanism does not pose a high resistance when the threadedly engageable cylinder is turned in the tightening direction. Moreover, even if a rotary torque in the tightening direction or the loosening direction is applied to the threadedly engageable cylinder, the strength of the elastic leaf of the loosening prevention mechanism can be maintained.

MODE FOR CARRYING OUT THE INVENTION

Figure 13:
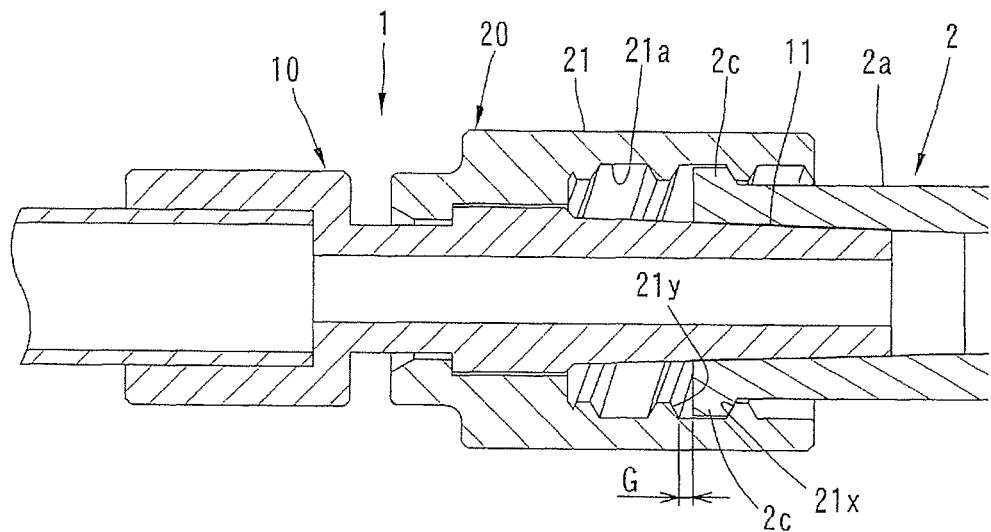
FIG. 13 is a longitudinal sectional view of a conventional connecting structure for medical use including a male connecting device and a female connector in a state where joining of a male luer portion and a female luer portion is completed by tightening a threadedly engageable cylinder.
Figure 14:
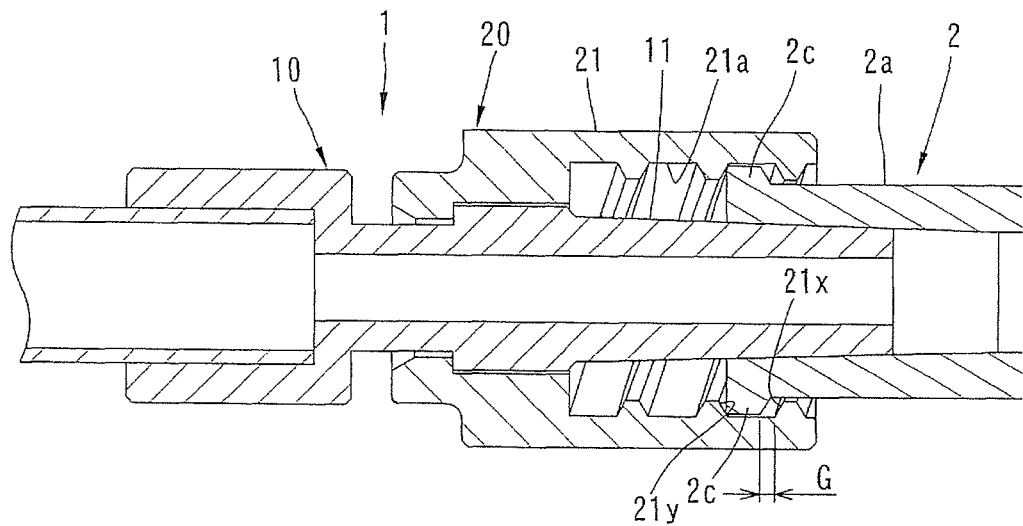
FIG. 14 is a longitudinal sectional view of the conventional connecting structure for medical use, in a state where the threadedly engageable cylinder is loosened with respect to a male connector.

A male connecting device for medical use according to a first embodiment of the present invention will be described hereinafter with reference to FIGS. 1 to 10. In this embodiment, same reference numerals are used to indicate components corresponding to those of a prior art device shown in FIGS. 13 and 14.

Figure 1:
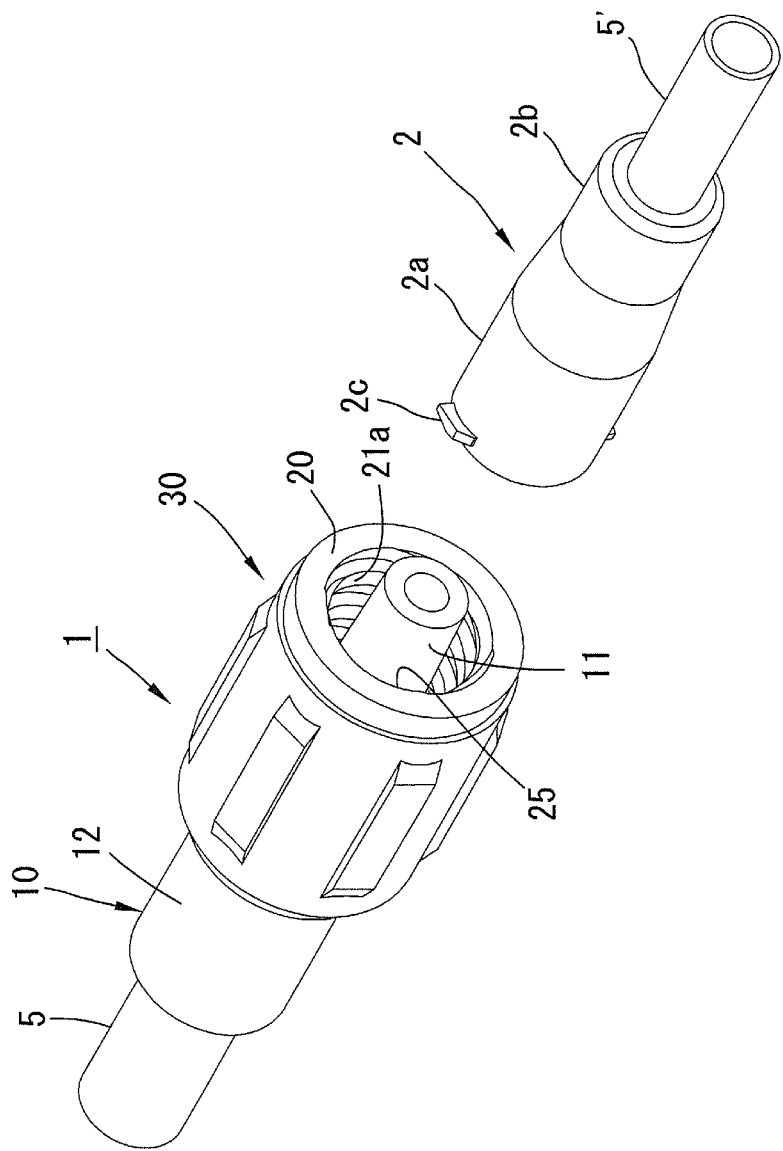
FIG. 1 is a perspective view of a male connecting device for medical use according to a first embodiment of the present invention and a female connector.

As shown in FIG. 1, a male connecting device 1 cooperates with a female connector 2 to connect tubes 5, 5' (first and second medical components) in which liquid such as medical solution and blood is to be flown. Components of the male connecting device 1 and the female connector 2 are made of resin.

The female connector 2 having a simpler structure will be described first with reference to FIGS. 1 and 2B. The female connector 2 having a thin and long cylindrical configuration includes a female luer portion 2a in one end portion (distal end portion) thereof in an axial direction and a coupling portion 2b in the other end portion (basal end portion) thereof. An inner surface of the female luer portion 2a has a gently tapered configuration whose diameter is gradually increased towards a distal end thereof. A pair of engageable protrusions 2c that work as male screws are formed in an outer periphery of a distal end portion of the female luer portion 2a 180 degrees apart from each other in a circumferential direction. An end portion of the tube 5' is to be inserted into and fixed at the coupling portion 2b.

As shown in FIGS. 2A and 3 to 5, the male connecting device 1 includes a male connector 10, a threadedly engageable cylinder 20 and an operation cylinder 30. The threadedly engageable cylinder 20 is mounted on an outer periphery of the male connector 10 such that the threadedly engageable cylinder 20 is rotatable but immovable in an axial direction. The operation cylinder 30 is mounted on an outer periphery of the threadedly engageable cylinder 20 such that the operation cylinder 30 is rotatable but immovable in the axial direction.

Figure 6A:
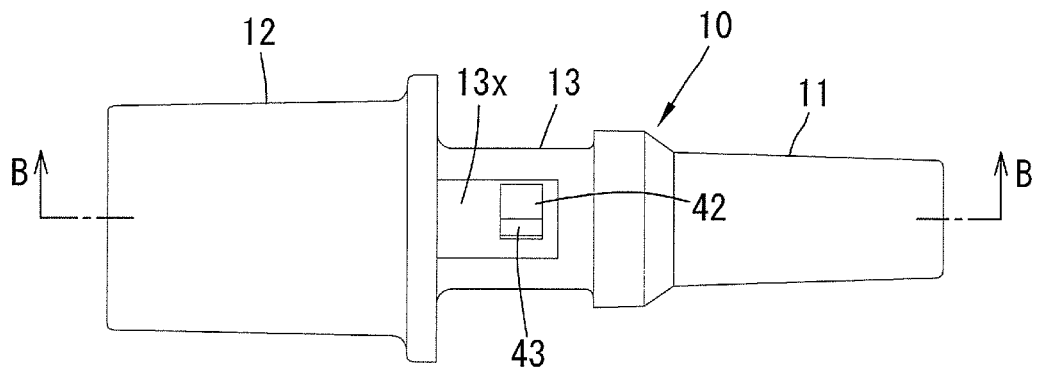
FIG. 6A is a plan view of a male connector of the male connecting device.
Figure 6B:
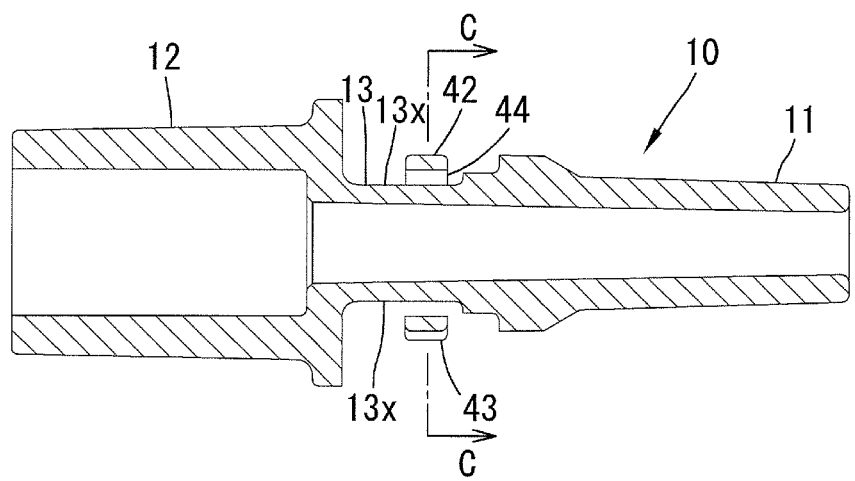
FIG. 6B is a cross-sectional view taken along line B-B of FIG. 6A.
Figure 6C:
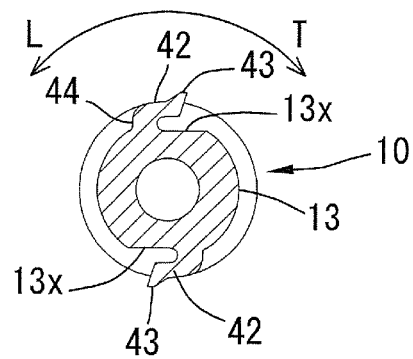
FIG. 6C is a cross-sectional view taken along line C-C of FIG. 6B.

As shown in FIGS. 6A and 6B, the male connector 10 has a thin and long cylindrical configuration. The male connector 10 includes a male luer portion 11 in one end portion (distal end portion) thereof in an axial direction, a coupling portion 12 in the other end portion (basal end portion) thereof and a support portion 13 in a middle portion thereof. An outer surface of the male luer portion 11 has a gently tapered configuration whose diameter is gradually reduced towards a distal end thereof. A taper angle of the outer surface of the male luer portion 11 and a taper angle of the inner surface of the female luer portion 2a are substantially the same. An end portion of the tube 5 is to be inserted into and fixed at the coupling portion 12.

Figure 2A:
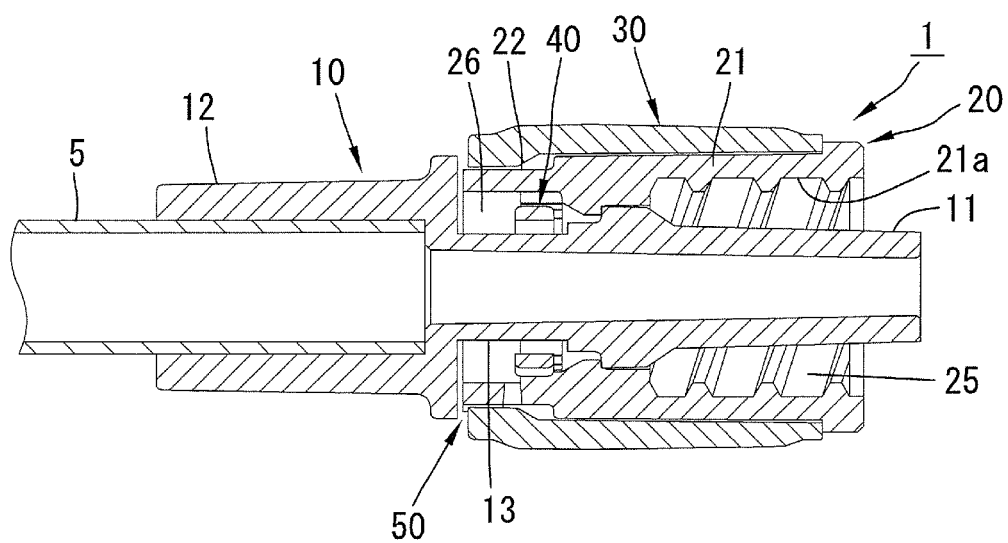
FIG. 2A is a longitudinal sectional view of the male connecting device.
Figure 7A:
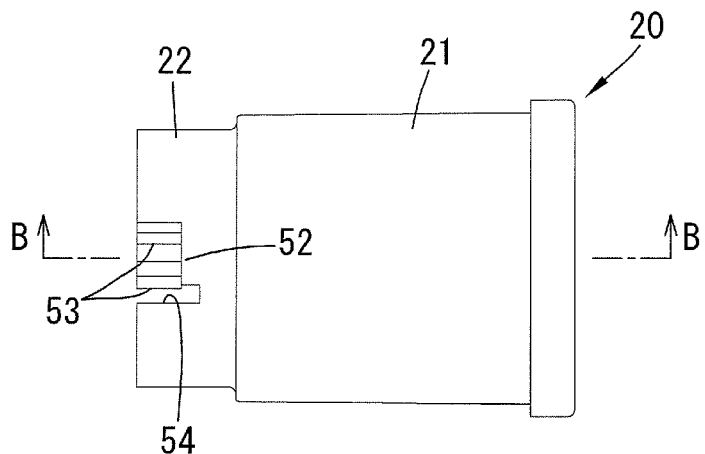
FIG. 7A is a plan view of a threadedly engageable cylinder of the male connecting device.
Figure 7B:
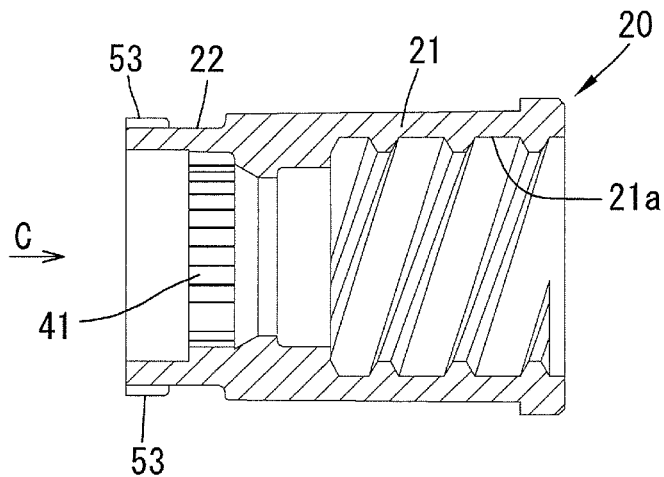
FIG. 7B is a cross-sectional view taken along line B-B of FIG. 7A.

As shown in FIGS. 7A and 7B, the threadedly engageable cylinder 20 includes a threadedly engageable portion 21 in one end portion (distal end portion) thereof in the axial direction and a mounting portion 22 in the other end portion (basal end portion) thereof. A female screw 21a is formed in an inner periphery of the threadedly engageable portion 21. As shown in FIG. 2A, the mounting portion 22 is mounted on the support portion 13 of the male connector 10 such that the mounting portion 22 is rotatable but immovable in the axial direction.

As shown in FIGS. 1 and 2A, in a state where the threadedly engageable cylinder 20 is mounted on the male connector 10, the threadedly engageable portion 21 of the threadedly engageable cylinder 20 is disposed outside of the male luer portion 11 in a radial direction and an annular insertion space 25 is formed between the threadedly engageable portion 21 and the male luer portion 11. An annular gap 26 is formed between a small-diameter portion of the support portion 13 of the male connector 10 and the mounting portion 22 of the threadedly engageable cylinder 20.

Figure 5:
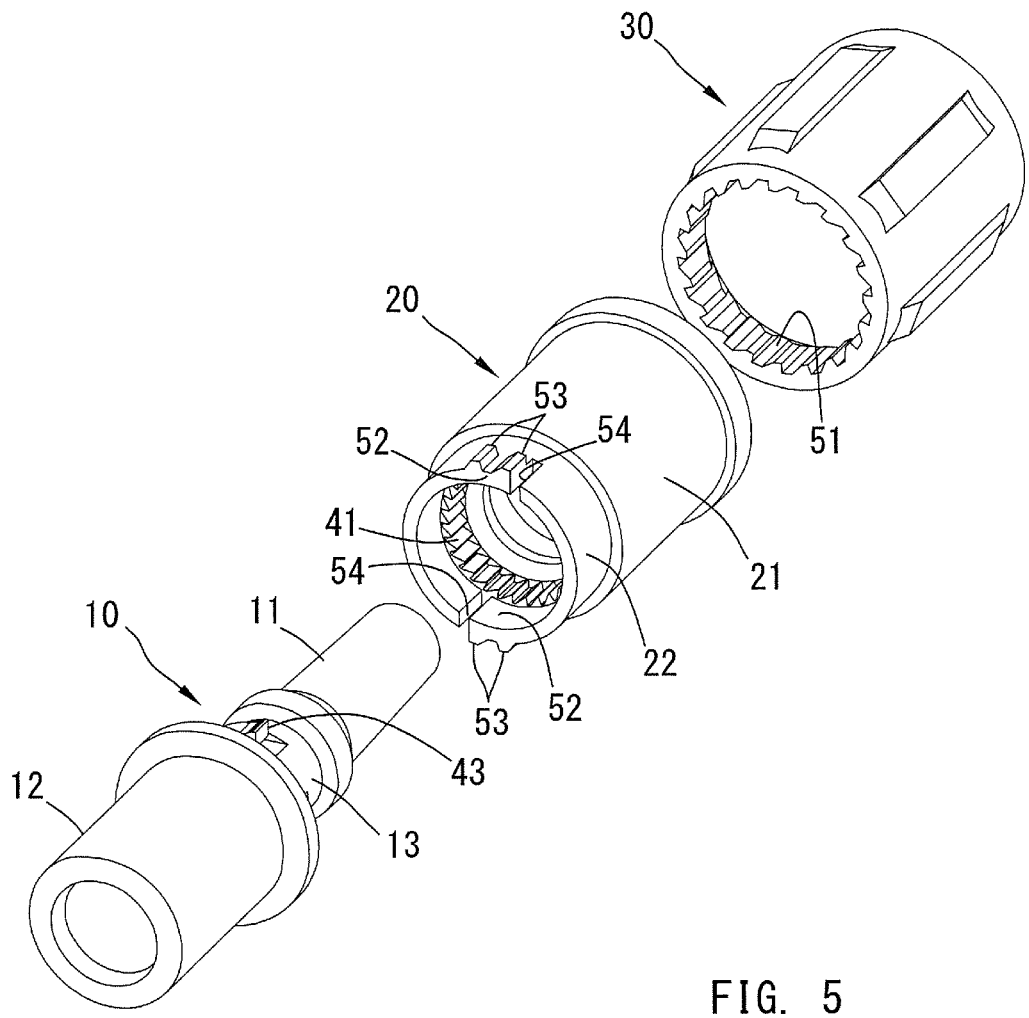
FIG. 5 is an exploded perspective view of the male connecting device, viewed from the same direction as FIG. 4.
Figure 7C:
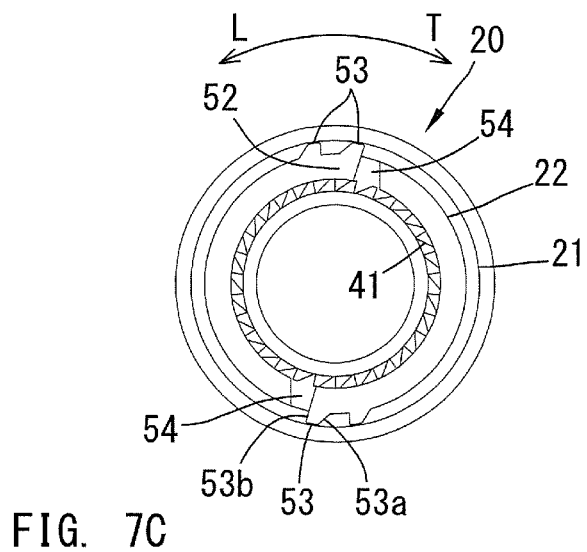
FIG. 7C is a view from direction C of FIG. 7B.

As shown in FIG. 2A, the male connecting device 1 includes a loosening prevention mechanism 40 disposed in the annular gap 26. The loosening prevention mechanism 40 includes ratchet teeth 41 and a pair of elastic leaves 42. As shown in FIGS. 5, 7B and 7C, the ratchet teeth 41 are formed in an inner periphery of the mounting portion 22 of the threadedly engageable cylinder 20 over an entire periphery. As shown in FIGS. 3 and 6A to 6C, the elastic leaves 42 are formed in the small-diameter portion of the support portion 13 of the male connector 10.

Figure 10A:
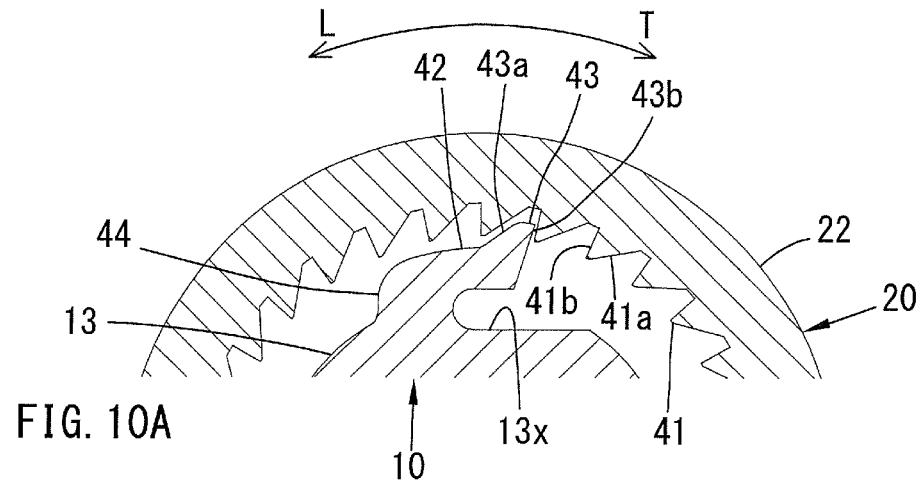
FIG. 10A is an enlarged cross-sectional view of a major portion of a loosening prevention mechanism of FIG. 9 in a state where a rotary torque is not applied to the threadedly engageable cylinder.

The ratchet teeth 41 are formed in the mounting portion 22 of the threadedly engageable cylinder 20 at a portion spaced from a basal end of the mounting portion 22 through a predetermined distance. As shown in FIG. 10A, each tooth of the ratchet teeth 41 includes an inclined surface 41a on a tightening direction T side to be described later and a steep surface 41b on a loosening direction L side.

A pair of chamfered flat surfaces 13x are formed in a circular cylindrical outer surface of the small-diameter portion of the support portion 13 of the male connector 10. The pair of flat surfaces 13x are opposed to each other in the radial direction and extend parallel to each other.

A support protrusion 44 is protruded outward in the radial direction from an end portion of the flat surface 13x of the support portion 13 in a circumferential direction (end portion on the loosening direction L side). The elastic leaf 42 extends from a distal end of the support protrusion 44 in the tightening direction T (circumferential direction) generally in parallel to the flat surface 13x. The support protrusion 44 and the elastic leaf 42 are arranged in a generally L-shaped configuration. The elastic leaf 42 is spaced from the flat surface 13x. An engageable claw 43 protruded outward in the radial direction is formed in a distal end (free end) of the elastic leaf 42.

Figure 9:
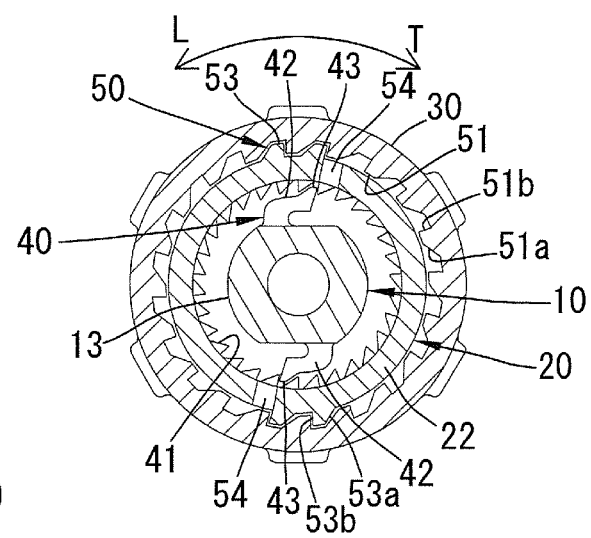
FIG. 9 is a cross-sectional view taken along line IX-IX of FIG. 2B.

As shown in FIGS. 9 and 10A, the pair of engageable claws 43 are engaged with the ratchet teeth 41. As shown in FIG. 10A, the engageable claw 43 includes an inclined surface 43a on the loosening direction L side and a steep surface 43b on the tightening direction T side. The inclined surface 43a of the engageable claw 43 and the inclined surface 41a of a corresponding tooth of the ratchet teeth 41 are opposed to each other in the circumferential direction and the steep surfaces 41b, 43b are opposed to each other in the circumferential direction.

Figure 3:
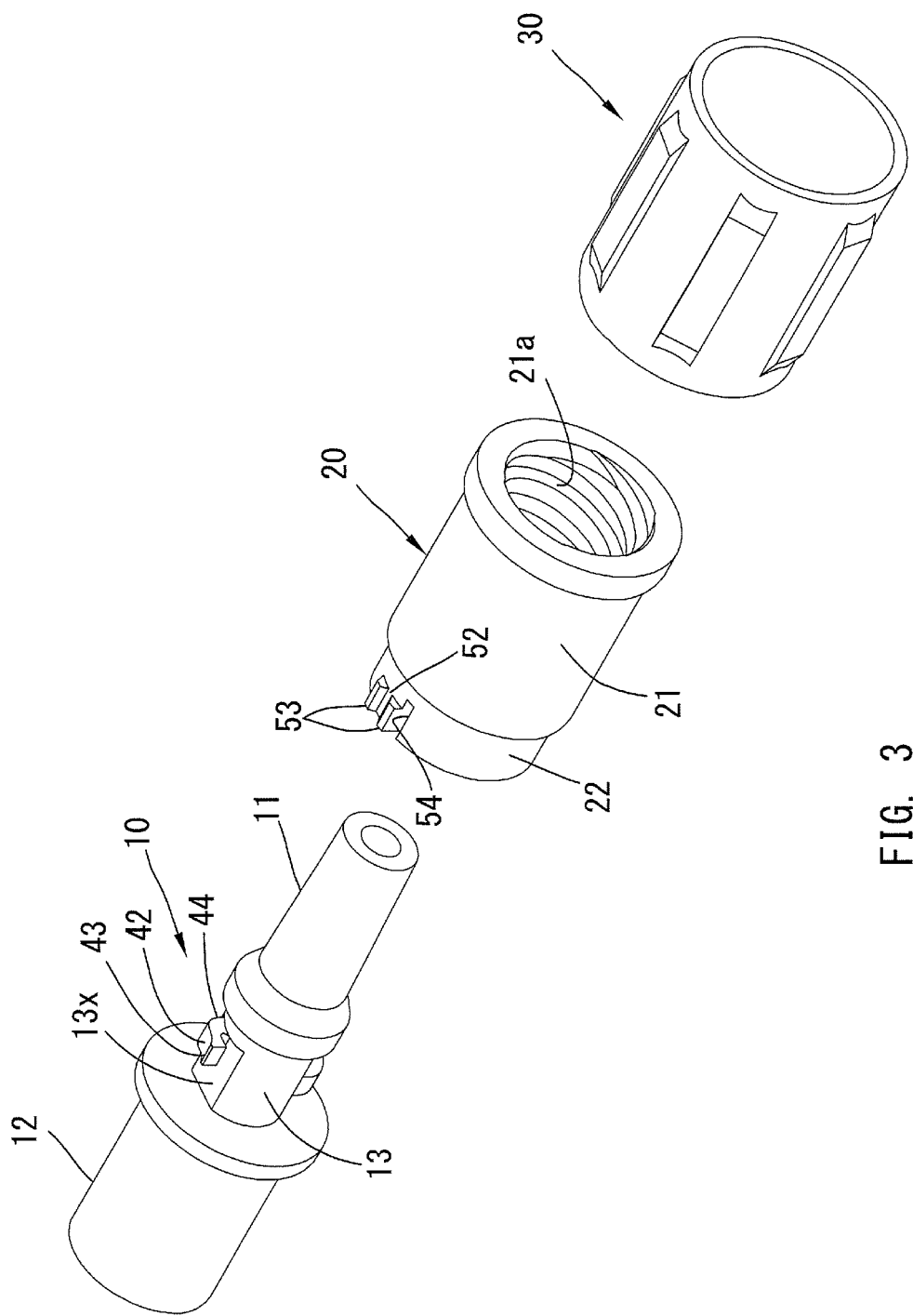
FIG. 3 is an exploded perspective view of the male connecting device.
Figure 4:
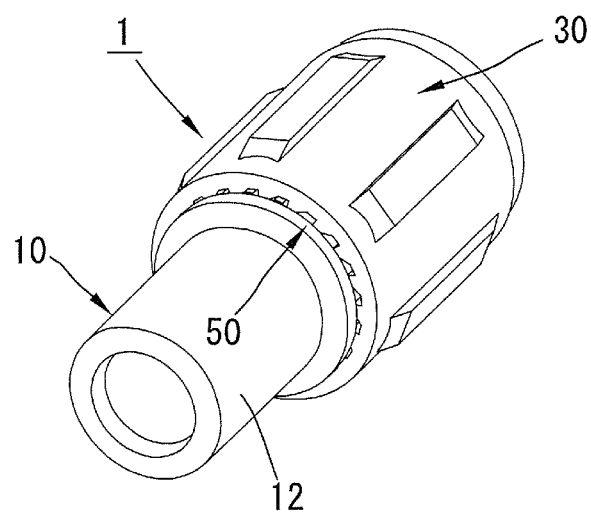
FIG. 4 is a perspective view of the male connecting device, viewed from a different direction from FIG. 1.
Figure 8A:
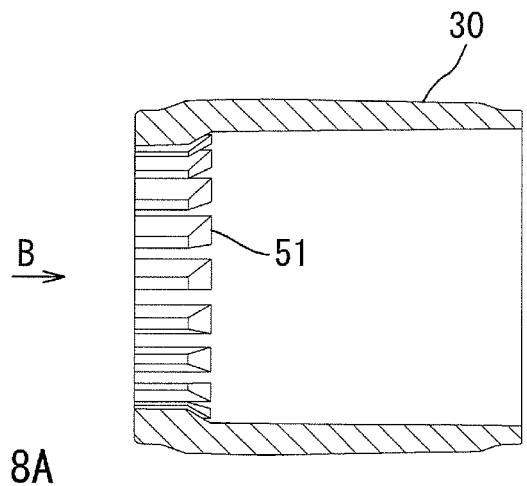
FIG. 8A is a longitudinal sectional view of an operation cylinder of the male connecting device.

As shown in FIG. 2A, the male connecting device 1 of this embodiment also includes a torque limiting mechanism 50 disposed between the threadedly engageable cylinder 20 and the operation cylinder 30. The torque limiting mechanism 50 includes engageable teeth 51 and a pair of elastically deformable portions 52. As shown in FIGS. 5 and 8, the engageable teeth 51 are formed in an inner periphery of a basal end portion of the operation cylinder 30 over an entire periphery. As shown in FIGS. 3, 5 and 7, the elastically deformable portions 52 are formed in the basal end portion of the threadedly engageable cylinder 20.

Figure 8B:
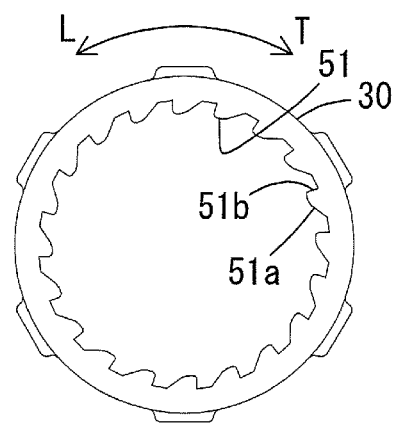
FIG. 8B is a view from direction B of FIG. 8A.

As shown in FIGS. 8B and 9, each tooth of the engageable teeth 51 includes an inclined surface 51a on the tightening direction T side and a steep surface 51b on the loosening direction L side as with the tooth of the ratchet teeth 41 of the loosening prevention mechanism 40.

As shown in FIGS. 3, 5 and 7, a pair of slits 54 are formed in an end portion of the mounting portion 22 of the threadedly engageable cylinder 20 180 degrees apart from each other in the circumferential direction. The slit 54 extends from an end of the mounting portion 22 in the axial direction. An area adjacent to the slit 54 is provided as the elastically deformable portion 52. The elastically deformable portion 52 is disposed adjacent to the ratchet teeth 41 of the loosening prevention mechanism 40 in the axial direction. An elastic coefficient of the elastically deformable portion 52 is much higher than that of the elastic leaf 42 of the loosening prevention mechanism 40.

An engageable claw 53 (second engageable claw) is formed in an outer surface of the elastically deformable portion 52 at a location adjacent to the slit 54. Another engageable claw 53 (second engageable claw) is formed at a location spaced from the engageable claw 53 in the circumferential direction through a distance corresponding to one pitch of the engageable teeth 51. As shown in FIG. 9, the engageable claws 53 are protruded outward in the radial direction and engaged with corresponding teeth of the engageable teeth 51.

The engageable claw 53, as with the engageable claw 43 of the loosening prevention mechanism 40, includes an inclined surface 53a on the loosening direction L side and a steep surface 53b on the tightening direction T side. In an engaged state, the inclined surface 53a of the engageable claw 53 and the inclined surface 51a of a corresponding tooth of the engageable teeth 51 are opposed to each other in the circumferential direction and the steep surfaces 51b, 53b are opposed to each other in the circumferential direction.

The female connector 2 is brought closer to the male connecting device 1 having the features mentioned above and the male luer portion 11 is inserted into the female luer portion 2a. The insertion proceeds without resistance until the engageable protrusions 2c of the female connector 2 are abutted against the female screw 21a of the threadedly engageable cylinder 20 of the male connecting device 1.

Next, when the operation cylinder 30 is turned in the tightening direction T, a torque of the operation cylinder 30 is transmitted to the threadedly engageable cylinder 20 via the torque limiting mechanism 50. Since the elastic coefficient of the elastically deformable portion 52 of the torque limiting mechanism 50 is high, the engageable claws 53 and the corresponding teeth of the engageable teeth 51 are maintained in engaged states with the inclined surfaces 53a of the engageable claws 53 and the inclined surfaces 51a of the corresponding teeth of the engageable teeth 51 of the torque limiting mechanism 50 abutted against one another. Therefore, the operation cylinder 30 and the threadedly engageable cylinder 20 are turned together.

Figure 10B:
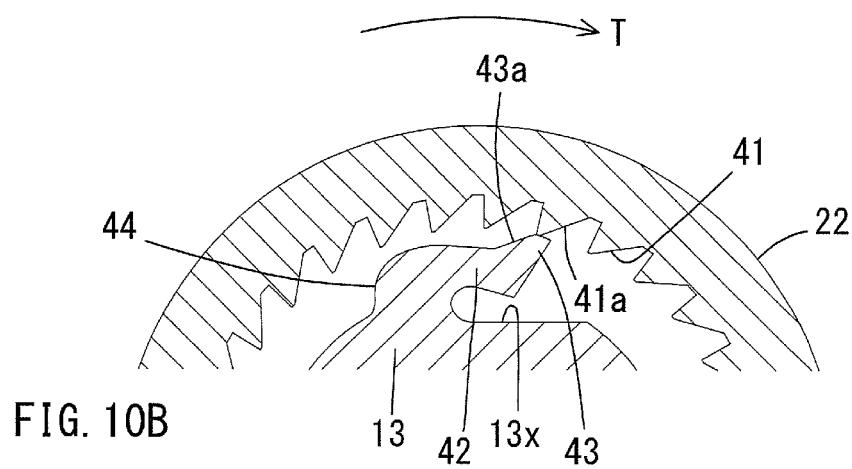
FIG. 10B is an enlarged cross-sectional view of the major portion of the loosening prevention mechanism in a state where a rotary torque in a tightening direction is applied to the threadedly engageable cylinder.

As mentioned above, when the threadedly engageable cylinder 20 is turned in the tightening direction T, the inclined surfaces 43a of the engageable claws 43 of the loosening prevention mechanism 40 slide on the inclined surfaces 41a of the corresponding teeth of the ratchet teeth 41 as shown in FIG. 10B. Therefore, the engageable claws 43 can be moved over the ratchet teeth 41 of the threadedly engageable cylinder 20. Since this movement is accompanied by elastic deformations of the elastic leaves 42 inward in the radial direction, the threadedly engageable cylinder 20 can be turned with respect to the male connector 10 without receiving much resistance from the loosening prevention mechanism 40.

By turning the threadedly engageable cylinder 20 in the tightening direction T as mentioned above, the threaded engagement between the female screw 21a and the engageable protrusions 2c proceeds, and the male luer portion 11 and the female luer portion 2a are joined with a pressing force working therebetween. Thereby, the male luer portion 11 and the female luer portion 2a can be joined with sufficient sealing properties. In this condition, as shown in FIG. 2B, a surface 21x on a deeper side of a screw thread of the female screw 21a of the threadedly engageable cylinder 20 is abutted against the engageable protrusion 2c of the female connector 2.

When the operation cylinder 30 is turned further, it encounters a strong resistance from a portion where the male luer portion 11 and the female luer portion 2a are joined, and a rotary torque exceeds a predetermined torque. Then, the inclined surfaces 53a of the engageable claws 53 slide on the inclined surfaces 51a of corresponding teeth of the engageable teeth 51, and the engageable claws 53 are moved over the engageable teeth 51 of the operation cylinder 30 accompanied by an elastic deformation of the elastically deformable portion 52 inward in the radial direction. Since the operation cylinder 30 is turned idly with respect to the threadedly engageable cylinder 20 as mentioned above, the rotary torque of the operation cylinder 30 is not transmitted to the threadedly engageable cylinder 20. Therefore, excessive torque is not applied to the threadedly engageable cylinder 20, thereby preventing the pressing force between the male luer portion 11 and the female luer portion 2a from becoming excessive. As a result, breakage of the male luer portion 11 and the female luer portion 2a can be prevented, and the male luer portion 11 and the female luer portion 2a can be prevented from being inseparably locked with each other.

Figure 10C:
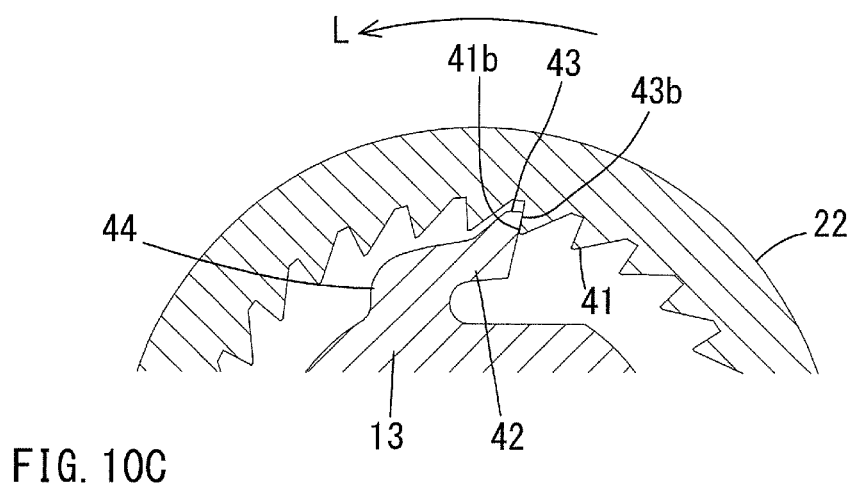
FIG. 10C is an enlarged cross-sectional view of the major portion of the loosening prevention mechanism in a state where a rotary torque in a loosening direction is applied to the threadedly engageable cylinder.

As shown in FIG. 10C, even when an unintentional torque in the loosening direction L is applied to the threadedly engageable cylinder 20 in the joined condition mentioned above, the threadedly engageable cylinder 20 is prohibited from rotating in the loosening direction with respect to the male connector 10. It is because the steep surfaces 41b of the ratchet teeth 41 are caught by the steep surfaces 43b of the engageable claws 43.

Figure 2B:
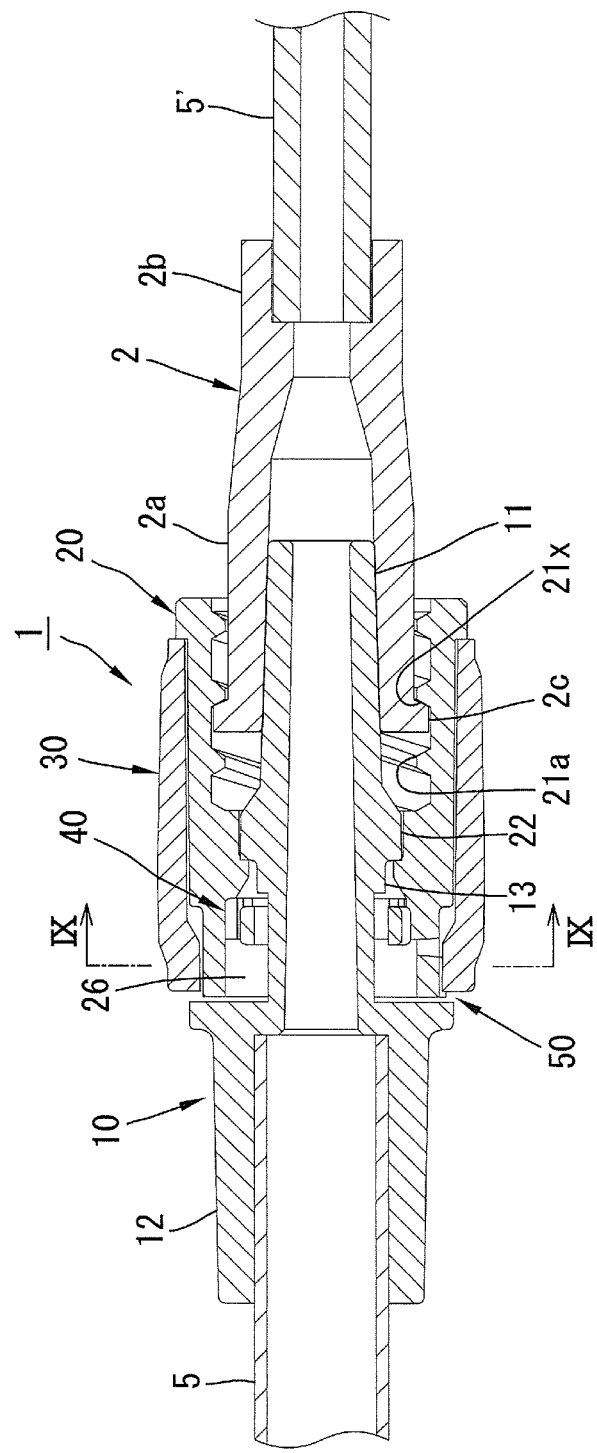
FIG. 2B is a longitudinal sectional view of the male connecting device, shown in a joined state with the female connector.

Since the threadedly engageable cylinder 20 is not rotated in the loosening direction with respect to the male connector 10 after the joining of the male luer portion 11 and the female luer portion 2a is completed as mentioned above, the surface 21x on the deeper side of the screw thread of the female screw 21a of the threadedly engageable cylinder 20 is maintained in the abutted state against the engageable protrusion 2c of the female connector 2 as shown in FIG. 2B. As a result, the female luer portion 2a and the male luer portion 11 are not displaced in a direction away from each other even when a pressure of fluid is high, and sufficient sealing properties can be maintained. Thereby, leakage of the fluid can be prohibited.

To disconnect the tubes 5, 5' after connecting them in this manner, the operation cylinder 30 is turned in the loosening direction L. Then, in the torque limiting mechanism 50, the steep surfaces 53b of the engageable claws 53 of the threadedly engageable cylinder 20 are abutted against the steep surfaces 51b of the corresponding teeth of the engageable teeth 51 of the operation cylinder 30, and the threadedly engageable cylinder 20 is rotated in the loosening direction together with the operation cylinder 30. At the same time, in the loosening prevention mechanism 40, the steep surfaces 43b of the engageable claws 43 of the male connector 10 are abutted against the steep surfaces 41b of the corresponding teeth of the ratchet teeth 41 of the threadedly engageable cylinder 20, and the male connector 10 is also rotated together with the threadedly engageable cylinder 20. As a result, the male luer portion 11 and the female luer portion 2b are released from the joined state.

Since the elastic leaf 42 of the loosening prevention mechanism 40 extends in the circumferential direction in this embodiment, the following advantages are provided.

As mentioned above, when a rotary torque in the loosening direction L is applied to the threadedly engageable cylinder 20, the steep surfaces 43b of the engageable claws 43 catch the steep surfaces 41b of the corresponding teeth of the ratchet teeth 41, and a force in the circumferential direction works on the elastic leaf 42. Also when a rotary torque in the tightening direction T is applied to the threadedly engageable cylinder 20, a force in the circumferential direction works on the elastic leaf 42 because of a friction generated between the inclined surfaces 43a of the engageable claws 43 and the inclined surfaces 41a of the corresponding teeth of the ratchet teeth 41. Since the elastic leaves 42 extend in the circumferential direction, the elastic leaves are not twisted by the force in the circumferential direction as mentioned above. Thereby, strength of the elastic leaves 42 can be maintained.

Since the elastic leaves 42 extend in the tightening direction T in the circumferential direction in this embodiment, the elastic leaves 42 can be easily elastically deformed when a rotary torque in the tightening direction T is applied to the threadedly engageable cylinder 20. Thereby, the joining can be performed easily. When a rotary torque in the loosening direction L is applied to the threadedly engageable cylinder 20, a force in a direction to raise the elastic leaf 42 is applied to the elastic leaf 42 via the engageable claw 43. Thereby, the engagements of the engageable claws 43 and the ratchet teeth 41 are deepened, and the threadedly engageable cylinder 20 can be surely prevented from loosening with respect to the male connector 10 of the threadedly engageable cylinder 20.

In this embodiment, a support protrusion 44 protruded outward in the radial direction from the outer periphery of the support portion 13 of the male connector 10 is formed. The elastic leaf 42 extends from the distal end of the support protrusion 44 in the circumferential direction. Since the elastic leaf 42 is elastically deformed inward in the radial direction generally about a portion where the support protrusion 44 and the elastic leaf 42 cross each other, the resistance that may generated when the threadedly engageable cylinder 20 is turned in the tightening direction T can be reduced further.

Since the elastic leaf 42 is disposed along the flat surface 13x of the support portion 13 of the male connector 10 in this embodiment, the elastic leaf 42 can be elastically deformed inward in the radial direction without being much protruded from the support portion 13 outward in the radial direction.

Figure 11:
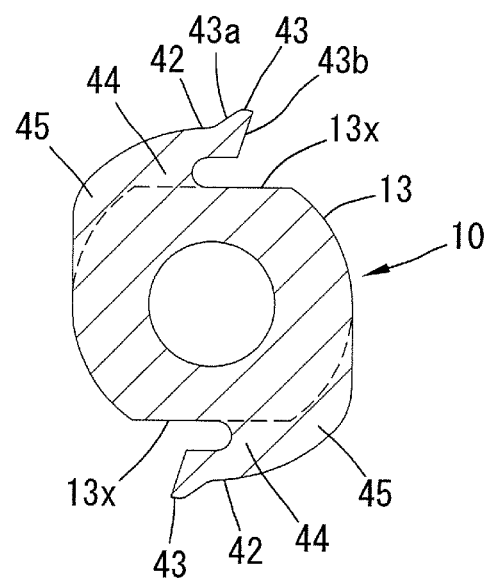
FIG. 11 is a view of a second embodiment of the present invention, corresponding to FIG. 6C.
Figure 12:
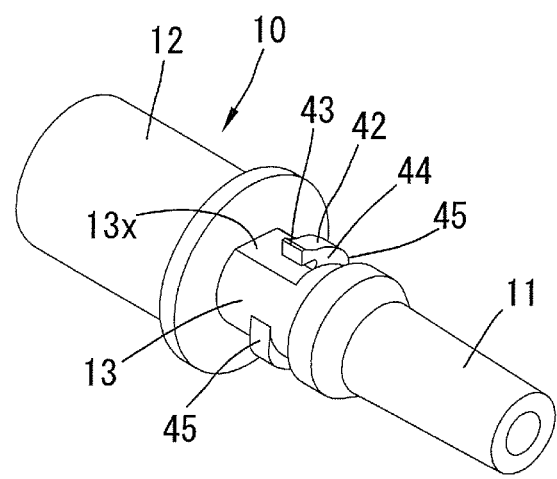
FIG. 12 is a perspective view of a male connector of the second embodiment.

Next, a second embodiment of the present invention will be described with reference to FIGS. 11 and 12. Components of this embodiment are same as those of the first embodiment except a major portion of a male connector 10. The male connector 10 of this embodiment has a reinforcement raised portion 45 formed in an outer periphery of a small-diameter portion of a support portion 13. The reinforcement raised portion 45 continues to a support protrusion 44 on an opposite side to an elastic leaf 42.

In this embodiment, even when a strong rotary torque works on a threadedly engageable cylinder 20 and a strong force towards the support protrusion 44 is applied to the elastic leaf 42, the force can be received by the reinforcement raised portion 45. Thereby, strengths of the elastic leaf 42 and the support protrusion 44 can be surely maintained.

The present invention is not limited to the embodiments described above and various modifications can be made.

The elastic leaf of the loosening prevention mechanism may extend in the loosening direction in the circumferential direction.

The operation cylinder and the torque limiting mechanism may be omitted.

The support portion and the coupling portion of the male connector may be separate from each other and rotatable with respect to each other.

The present invention may be applied for connecting a three-way stopcock and a tube. The present invention may be applied for connecting various kinds of medical components.

INDUSTRIAL APPLICABILITY

The present invention may be applied to a male connecting device used for a connecting structure for medical use.

The invention claimed is:

1. A male connecting device for medical use comprising:
a male connector having a cylindrical configuration; and
a threadedly engageable cylinder rotatably coupled to the male connector,
the male connector including a male luer portion and a support portion arranged in a direction from a distal end to a basal end thereof in this order,
the threadedly engageable cylinder including a threadedly engageable portion and a mounting portion arranged in a direction from a distal end to a basal end thereof in this order,
the mounting portion of the threadedly engageable cylinder rotatably mounted on an outer periphery of the support portion of the male connector, the threadedly engageable portion including a female screw in an inner periphery thereof, the threadedly engageable portion disposed outside of the male luer portion in a radial direction, wherein
the male connecting device further comprises a loosening prevention mechanism disposed between the male connector and the threadedly engageable cylinder, the loosening prevention mechanism prohibits the threadedly engageable cylinder from rotating in a loosening direction with respect to the male connector, wherein
the loosening prevention mechanism includes ratchet teeth formed in an inner periphery of the threadedly engageable cylinder over an entire periphery, at least one elastic leaf formed in an outer periphery of the male connector so as to extend in a circumferential direction with a free end thereof spaced from the outer periphery of the male connector and an engageable claw formed in the free end of the elastic leaf so as to be protruded outward in a radial direction, wherein
when the threadedly engageable cylinder receives a rotary torque in a tightening direction, the engageable claw is moved over the ratchet teeth accompanied by an elastic deformation of the elastic leaf inward in the radial direction, thereby allowing the threadedly engageable cylinder to be rotated with respect to the male connector, and
when the threadedly engageable cylinder receives a rotary torque in the loosening direction, the engageable claw catches the ratchet teeth, thereby prohibiting the threadedly engageable cylinder from rotating with respect to the male connector,
the male connecting device for medical use further comprising an operation cylinder rotatably mounted on an outer periphery of the threadedly engageable cylinder and a torque limiting mechanism disposed between the threadedly engageable cylinder and the operation cylinder, wherein
the torque limiting mechanism transmits a rotary torque of the operation cylinder in a tightening direction to the threadedly engageable cylinder, the torque limiting mechanism allows the operation cylinder to be turned idly with respect to the threadedly engageable cylinder when the rotary torque exceeds a predetermined torque,
the torque limiting mechanism includes engageable teeth formed in an inner periphery of the operation cylinder over an entire periphery, at least one elastically deformable portion formed in the threadedly engageable cylinder and a second engageable claw formed in the elastically deformable portion and protruded outward in the radial direction, the second engageable claw engageable with the engageable teeth, and an elastic coefficient of the elastically deformable portion is higher than an elastic coefficient of the elastic leaf of the loosening prevention mechanism.

2. The male connecting device for medical use according to claim 1, wherein the elastic leaf extends in the tightening direction of the threadedly engageable cylinder.

3. The male connecting device for medical use according to claim 1, wherein a support protrusion protruded outward in the radial direction is formed in the outer periphery of the male connector and the elastic leaf extends from a distal end of the support protrusion in the circumferential direction.

4. The male connecting device for medical use according to claim 3, wherein a chamfered flat surface is formed in the outer periphery of the male connector,
the support protrusion continues from an end portion of the flat surface in the circumferential direction, and the elastic leaf extends along the flat surface and is spaced from the flat surface.

5. The male connecting device for medical use according to claim 3, wherein a reinforcement raised portion that continues to the support protrusion is formed in the outer periphery of the male connector on an opposite side to the elastic leaf.

6. The male connecting device for medical use according to claim 1, wherein the elastically deformable portion is formed in an end portion of the mounting portion of the threadedly engageable cylinder and the ratchet teeth of the loosening prevention mechanism are formed in an inner periphery of the mounting portion at locations adjacent to the elastically deformable portion in an axial direction.

7. The male connecting device for medical use according to claim 1, wherein an annular gap is formed between the mounting portion of the threadedly engageable cylinder and the support portion of the male connector, and wherein the loosening prevention mechanism is disposed in the annular gap.

8. The male connecting device for medical use according to claim 1, wherein an annular gap is formed between the mounting portion of the threadedly engageable cylinder and the support portion of the male connector, wherein the loosening prevention mechanism is disposed in the annular gap, and
wherein the elastically deformable portion of the torque limiting mechanism formed in the threadedly engageable cylinder is elastically deformed radially inwardly toward the annular gap when the operating cylinder is turned idly.

* * * * *